United States Patent [19]

Cameron et al.

[11] Patent Number: 5,607,454
[45] Date of Patent: Mar. 4, 1997

[54] ELECTROTHERAPY METHOD AND APPARATUS

[75] Inventors: David Cameron, Seattle; Thomas D. Lyster, Bothell; Daniel J. Powers, Bainbridge Island; Bradford E. Gliner, Bellevue; Clinton S. Cole, Seattle; Carlton B. Morgan, Bainbridge Island, all of Wash.

[73] Assignee: Heartstream, Inc., Seattle, Wash.

[21] Appl. No.: 227,553

[22] Filed: Apr. 14, 1994

Related U.S. Application Data

[63] Continuation-in-part of Ser. No. 103,837, Aug. 6, 1993.

[51] Int. Cl.⁶ .................................................. A61N 1/39
[52] U.S. Cl. ...................... 607/5; 607/7; 607/6; 607/74; 607/62
[58] Field of Search .................................. 607/2, 4, 5–7, 607/62, 74

[56] References Cited

U.S. PATENT DOCUMENTS

| | | |
|---|---|---|
| 3,211,154 | 10/1965 | Becker et al. |
| 3,241,555 | 3/1966 | Caywood et al. |
| 3,706,313 | 12/1972 | Milani et al. |
| 3,782,389 | 1/1974 | Bell ............................................. 607/8 |
| 3,860,009 | 1/1975 | Bell et al. ................................... 607/8 |
| 3,862,636 | 1/1975 | Bell et al. ................................... 607/5 |
| 3,886,950 | 6/1975 | Ukkestad et al. ........................... 607/5 |

(List continued on next page.)

FOREIGN PATENT DOCUMENTS

| | | |
|---|---|---|
| 0281219 | 9/1988 | European Pat. Off. |
| 0315368 | 5/1989 | European Pat. Off. |
| 0353341 | 2/1990 | European Pat. Off. |
| 0437104 | 7/1991 | European Pat. Off. |
| 0507504 | 10/1992 | European Pat. Off. |
| 2070435 | 9/1981 | United Kingdom |
| 2083363 | 3/1982 | United Kingdom |
| WO93/16759 | 9/1993 | WIPO |
| WO94/21327 | 9/1994 | WIPO |
| WO94/22530 | 10/1994 | WIPO |

OTHER PUBLICATIONS

Alferness et al., "The influence of shock waveforms on defibrillation efficacy," *IEEE Engineering in Medicine and Biology*, pp. 25–27 (Jun. 1990).

Anderson et al., "The efficacy of trapezoidal wave forms for ventricular defibrillation," *Chest*, 70(2):298–300 (1976).

Blilie et al., "Predicting and validating cardiothoracic current flow using finite element modeling," *PACE*, 15:563, abstract 219 (Apr. 1992).

(List continued on next page.)

*Primary Examiner*—Marvin M. Lateef
*Assistant Examiner*—Kennedy J. Schaetzle
*Attorney, Agent, or Firm*—Morrison & Foerster

[57] ABSTRACT

An electrotherapy method and apparatus for delivering a multiphasic waveform from an energy source to a patient. The preferred embodiment of the method comprises the steps of charging the energy source to an initial level; discharging the energy source across the electrodes to deliver electrical energy to the patient in a multiphasic waveform; monitoring a patient-dependent electrical parameter during the discharging step; shaping the waveform of the delivered electrical energy based on a value of the monitored electrical parameter, wherein the relative duration of the phases of the multiphasic waveform is dependent on the value of the monitored electrical parameter. The preferred apparatus comprises an energy source; two electrodes adapted to make electrical contact with a patient; a connecting mechanism forming an electrical circuit with the energy source and the electrodes when the electrodes are attached to a patient; and a controller operating the connecting mechanism to deliver electrical energy from the energy source to the electrodes in a multiphasic waveform the relative phase durations of which are based on an electrical parameter monitored during delivery of the electrical energy. The preferred defibrillator apparatus weighs less than 4 pounds and has a volume less than 150 cubic inches, and most preferably, weighs approximately three pounds or less and has a volume of approximately 141 cu. in.

59 Claims, 4 Drawing Sheets

U.S. PATENT DOCUMENTS

| | | | |
|---|---|---|---|
| 4,023,573 | 5/1977 | Pantridge et al. | 607/5 |
| 4,328,808 | 5/1982 | Charbonnier et al. | |
| 4,419,998 | 12/1983 | Heath . | |
| 4,473,078 | 9/1984 | Angel | 607/6 |
| 4,494,552 | 1/1985 | Heath . | |
| 4,504,773 | 3/1985 | Suzuki et al. | |
| 4,574,810 | 3/1986 | Lerman . | |
| 4,595,009 | 6/1986 | Leinders . | |
| 4,610,254 | 9/1986 | Morgan et al. | |
| 4,619,265 | 10/1986 | Morgan et al. | |
| 4,637,397 | 1/1987 | Jones et al. | |
| 4,745,923 | 5/1988 | Winstrom . | |
| 4,800,883 | 1/1989 | Winstrom . | |
| 4,821,723 | 4/1989 | Baker, Jr. et al. | |
| 4,840,177 | 6/1989 | Charbonnier et al. | |
| 4,848,345 | 7/1989 | Zenkich . | |
| 4,850,357 | 7/1989 | Bach, Jr. . | |
| 4,953,551 | 9/1990 | Mehra et al. | |
| 4,998,531 | 3/1991 | Bocchi et al. | |
| 5,078,134 | 1/1992 | Heilman et al. | |
| 5,083,562 | 1/1992 | de Coriolis et al. | |
| 5,107,834 | 4/1992 | Ideker et al. | |
| 5,111,813 | 5/1992 | Charbonnier et al. | |
| 5,111,816 | 5/1992 | Pless et al. | |
| 5,207,219 | 5/1993 | Adams et al. | |
| 5,215,081 | 6/1993 | Ostroff . | |
| 5,222,480 | 6/1993 | Couche et al. | |
| 5,222,492 | 6/1993 | Morgan et al. | |
| 5,230,336 | 7/1993 | Fain et al. | 607/7 |
| 5,237,989 | 8/1993 | Morgan et al. | |
| 5,249,573 | 10/1993 | Fincke et al. | 607/6 |
| 5,275,157 | 1/1994 | Morgan et al. | |
| 5,306,291 | 4/1994 | Kroll et al. | |
| 5,334,219 | 8/1994 | Kroll . | |
| 5,352,239 | 10/1994 | Pless | 607/5 |
| 5,370,664 | 12/1994 | Morgan et al. | |
| 5,372,606 | 12/1994 | Lang et al. | 607/8 |

OTHER PUBLICATIONS

Chapman et al., "Non–thoracotomy internal defibrillation: Improved efficacy with biphasic shocks," *Circulation*, 76:312, abstract no. 1239 (1987).

Cooper et al., "Temporal separation of the two pulses of single capacitor biphasic and dual monophasic waveforms," *Circulation*, 84(4):612, abstract no. 2433 (1991).

Cooper et al., "The effect of phase separation on biphasic waveform defibrillation,"*PACE*, 16:471–482 (Mar. 1993).

Cooper et al., "The effect of temporal separation of phases on biphasic waveform defibrillation efficacy," *The Annual International Conference of the IEEE Engineering in Medicine and Biology Society*, 13(2):0766–0767 (1991).

Crampton et al., "Low–energy ventricular defibrillation and miniature defibrillators," *JAMA*, 235(21):2284 (1976).

Dahlbäck et al., "Ventricular defibrillation with square–waves," *The Lancet* (Jul. 2, 1966).

Echt et al., "Biphasic waveform is more efficacious than monophasic waveform for transthoracic cardioversion," *PACE*, 16:914, abstract no. 256 (Apr. 1993).

Feeser et al., "Strength–duration and probability of success curves for defibrillation with biphasic waveforms," *Circulation*, 82(6):2128–2141 (1990).

Guse et al., "Defibrillation with low voltage using a left ventricular catheter and four cutaneous patch electrodes in dogs," *PACE*, 14:443–451 (Mar. 1991).

Jones et al., "Decreased defibrillator–induced dysfunction with biphasic rectangular waveforms," *Am. J. Physiol.*, 247:H792–796 (1984).

Jones et al., "Defibrillator waveshape optimization," Devices and Tech. Meeting, NIH (1982).

Jones et al., "Improved defibrillator waveform safety factor with biphasic waveforms," *Am. J. Physiol.*, 245:H60–65 (1983).

Jones et al., "Reduced excitation threshold in potassium depolarized myocardial cells with symmetrical biphasic waveforms," *J. Mol. Cell. Cardiol.*, 17(39):XXVII, abstract no. 39 (1985).

Jude et al., "Fundamentals of Cardiopulmonary Resuscitation," F.A. Davis Company, Philadelphia PA, pp. 98–104 (1965).

Kerber et al., "Energy, current, and success in defibrillation and cardioversion: Clinical studies using an automated impedance–based method of energy adjustment," *Circulation*, 77(5):1038–1046 (1988).

Knickerbocker et al., "A portable defibrillator,"*IEEE Trans. on Power and Apparatus Systems*, 69:1089–1093 (1963).

Kouwenhoven, "The development of the defibrillator," *Annals of Internal Medicine*, 71(3):449–458 (1969).

Langer et al., "Considerations in the development of the automatic implantable defibrillator," *Medical Instrumentation*, 10(3):163–167 (1976).

Lerman et al. "Current–based versus energy–based ventricular defibrillation: A prospective study," *JACC*, 12(5):1259–1264 (1988).

Lindsay et al., "Prospective evaluation of a sequential pacing and high–energy bi–directional shock algorithm for transvenous cardioversion in patients with ventricular tachycardia," *Circulation*, 76(3):601–609 (1987).

Mirowski et al., "Clinical treatment of life threatening ventricular tachyarrhythmias with the automatic implantable defibrillator," *American Heart Journal*, 102(2):265–270 (1981).

Mirowski et al., "Termination of malignant ventricular arrhythmias with an implanted automatic defibrillator in human beings," *The New England Journal of Medicine*, 303(6):322–324 (1980).

Podolsky, "Keeping the beat alive," *U.S. News & World Report* (Jul. 22, 1991).

Product Brochure for First Medic Semi–Automatic Defibrillators (1994), Spacelabs Medical Products, 15220 N.E. 40th Street, P.O. Box 97013, Redmond, WA 98073–9713.

Product Brochure for the Shock Advisory System (1987), Physio–Control, 11811 Willows Road Northeast, P.O. Box 97006, Redmond, WA 98073–9706.

Redd (editor), "Defibrillation with biphasic waveform may increase safety, improve survival," *Medlines*, pp. 1–2 (Jun.–Jul. 1984).

Saksena et al., "A prospective evaluation of single and dual current pathways for transvenous cardioversion in rapid ventricular tachycardia," *PACE*, 10:1130–1141 (Sep.–Oct. 1987).

Saksena et al., "Developments for future implantable cardioverters and defibrillators," *PACE*, 10:1342–1358 (Nov.–Dec. 1987).

Schuder "The role of an engineering oriented medical research group in developing improved methods and devices for achieving ventricular defibrillation: The University of Missouri experience," *PACE*, 16:95–124 (Jan. 1993).

Schuder et al. "Comparison of effectiveness of relay–switched, one–cycle quasisinusoidal waveform with critically damped sinusoid waveform in transthoracic defibrillation of 100–kilogram calves," *Medical Instrumentation*, 22(6):281–285 (1988).

Schuder et al., "A multielectrode–time sequential laboratory defibrillator for the study of implanted electrode systems," *Amer. Soc. Artif. Int. Organs,* XVIII:514–519 (1972).

Schuder et al., "Defibrillation of 100 kg calves with asymmetrical, bi–directional, rectangular pulses," *Card. Res.,* 18:419–426 (1984).

Schuder et al., "Development of automatic implanted defibrillator," Devices & Tech. Meeting NIH (1981).

Schuder et al., "One–cycle bi–directional rectangular wave shocks for open chest defibrillation in the calf," *Abs. Am. Soc. Artif. Intern. Organs,* 9:16.

Schuder et al., "Transthoracic ventricular defibrillation in the 100 kg calf with symmetrical one–cycle bi–directional rectangular wave stimuli," *IEEE Trans. BME,* 30(7):415–422 (1983).

Schuder et al., "Transthoracic ventricular defibrillation with square–wave stimuli: One–half cycle, one–cycle, and multicycle waveforms," *Circ. Res.,* XV:258–264 (1964).

Schuder et al., "Ultrahigh–energy hydrogen thyratron/SCR bi–directional waveform defibrillator," *Med. & Biol. Eng. & Comput.,* 20:419–424 (1982).

Schuder et al., "Waveform dependency in defibrillating 100 kg Calves," Devices & Tech. Meeting NIH (1982).

Schuder et al., "Waveform dependency in defibrillation," Devices & Tech. Meeting NIH (1981).

Stanton et al., "Relationship between defibrillation threshold and upper limit of vulnerability in humans," *PACE,* 15:563, abstract 221 (Apr. 1992).

Tang et al., "Strength duration curve for ventricular defibrillation using biphasic waveforms," *PACE,* 10: abstract no. 49 (Aug. 1987).

Tang et al., "Ventricular defibrillation using biphasic waveforms of different phasic duration," *PACE,* 10: abstract no. 47 (Mar.–Apr. 1987).

Tang et al., "Ventricular defibrillation using biphasic waveforms: The importance of phasic duration," *JACC,* 13(1):207–214 (1989).

Walcott et al., "Comparison of monophasic, biphasic, and the edmark waveform for external defibrillation," *PACE,* 15:563, abstract 218 (Apr. 1992).

Wathen et al., "Improved defibrillation efficacy using four nonthoracotomy leads for sequential pulse defibrillation," *PACE,* 15:563, abstract 220 (Apr. 1992).

Wetherbee et al., "Subcutaneous patch electrode—A means to obviate thoracotomy for implantation of the automatic implantable cardioverter defibrillation system?" *Circ.,* 72:384, abstract no. 1536 (1985).

Winkle "The implantable defibrillator in ventricular arrhythmias," *Hospital Practice,* pp. 149–165 (Mar. 1983).

Winkle et al., "Improved low energy defibrillation efficacy in man using a biphasic truncated exponential waveform," *JACC,* 9(2):142A (1987).

Zipes, "Sudden cardiac death," *Circulation,* 85(1):160–166 (1992).

Product information for Model H MSA Portable Defibrillator (Bulletin No. 1108–2); 4 pp.

Product information for MSA Portable Defibrillator (Bulletin No. 1108–1); 4 pp.

ELECTROTHERAPY METHOD AND APPARATUS

CROSS REFERENCE TO RELATED APPLICATION

This application is a continuation-in-part of U.S. patent application Ser. No. 08/103,837 filed Aug. 6, 1993, the disclosure of which is incorporated herein by reference.

BACKGROUND OF THE INVENTION

This invention relates generally to an electrotherapy method and apparatus for delivering an electrical pulse to a patient's heart. In particular, this invention relates to a method and apparatus for shaping the electrical waveform delivered by the defibrillator based on an electrical parameter measured during delivery of the waveform. The invention also relates to a defibrillator design meeting certain threshold size and weight requirements.

Sudden cardiac death is the leading cause of death in the United States. Most sudden cardiac death is caused by ventricular fibrillation, in which the heart's muscle fibers contract without coordination, thereby interrupting normal blood flow to the body. The only effective treatment for ventricular fibrillation is electrical defibrillation, which applies an electrical shock to the patient's heart.

To be effective, the defibrillation shock must be delivered to the patient within minutes of the onset of ventricular fibrillation. Studies have shown that defibrillation shocks delivered within one minute after ventricular fibrillation begins achieve up to 100% survival rate. The survival rate falls to approximately 30% if 6 minutes elapse before the shock is administered. Beyond 12 minutes, the survival rate approaches zero.

One way of delivering rapid defibrillation shocks is through the use of implantable defibrillators. Implantable defibrillators are surgically implanted in patients who have a high likelihood of needing electrotherapy in the future. Implanted defibrillators typically monitor the patient's heart activity and automatically supply electrotherapeutic pulses directly to the patient's heart when indicated. Thus, implanted defibrillators permit the patient to function in a somewhat normal fashion away from the watchful eye of medical personnel. Implantable defibrillators are expensive, however, and are used on only a small fraction of the total population at risk for sudden cardiac death.

External defibrillators send electrical pulses to the patient's heart through electrodes applied to the patient's torso. External defibrillators are useful in the emergency room, the operating room, emergency medical vehicles or other situations where there may be an unanticipated need to provide electrotherapy to a patient on short notice. The advantage of external defibrillators is that they may be used on a patient as needed, then subsequently moved to be used with another patient.

However, because external defibrillators deliver their electrotherapeutic pulses to the patient's heart indirectly (i.e., from the surface of the patient's skin rather than directly to the heart), they must operate at higher energies, voltages and/or currents than implanted defibrillators. These high energy, voltage and current requirements have made existing external defibrillators large, heavy and expensive, particularly due to the large size of the capacitors or other energy storage media required by these prior art devices. The size and weight of prior art external defibrillators have limited their utility for rapid response by emergency medical response teams.

Defibrillator waveforms, i.e., time plots of the delivered current or voltage pulses, are characterized according to the shape, polarity, duration and number of pulse phases. Most current external defibrillators deliver monophasic current or voltage electrotherapeutic pulses, although some deliver biphasic sinusoidal pulses. Some prior art implantable defibrillators, on the other hand, use truncated exponential, biphasic waveforms. Examples of biphasic implantable defibrillators may be found in U.S. Pat. No. 4,821,723 to Baker, Jr., et al.; U.S. Pat. No. 5,083,562 to de Coriolis et al.; U.S. Pat. No. 4,800,883 to Winstrom; U.S. Pat. No. 4,850,357 to Bach, Jr.; U.S. Pat. No. 4,953,551 to Mehra et al.; and U.S. Pat. No. 5,230,336 to Fain et al.

Because each implanted defibrillator is dedicated to a single patient, its operating parameters, such as electrical pulse amplitudes and total energy delivered, may be effectively titrated to the physiology of the patient to optimize the defibrillator's effectiveness. Thus, for example, the initial voltage, first phase duration and total pulse duration may be set when the device is implanted to deliver the desired amount of energy or to achieve a desired start and end voltage differential (i.e., a constant tilt). Even when an implanted defibrillator has the ability to change its operating parameters to compensate for changes in the impedance of the defibrillators leads and/or the patient's heart (as discussed in the Fain patent), the range of potential impedance changes for a single implantation in a single patient is relatively small.

In contrast, because external defibrillator electrodes are not in direct contact with the patient's heart, and because external defibrillators must be able to be used on a variety of patients having a variety of physiological differences, external defibrillators must operate according to pulse amplitude and duration parameters that will be effective in most patients, no matter what the patient's physiology. For example, the impedance presented by the tissue between external defibrillator electrodes and the patient's heart varies from patient to patient, thereby varying the intensity and waveform shape of the shock actually delivered to the patient's heart for a given initial pulse amplitude and duration. Pulse amplitudes and durations effective to treat low impedance patients do not necessarily deliver effective and energy efficient treatments to high impedance patients.

External defibrillators may be subjected to extreme load conditions which could potentially damage the waveform generator circuits. For example, improperly applied defibrillator electrodes may create a very low impedance current path during the shock delivery, which could result in excessively high current within the waveform circuit. Thus, an external defibrillator has an additional design requirement to limit the peak current to safe levels in the waveform circuit, which is not normally a concern for implanted defibrillators.

Prior art defibrillators have not fully addressed the patient variability problem. One prior art approach to this problem was to provide an external defibrillator with multiple energy settings that could be selected by the user. A common protocol for using such a defibrillator was to attempt defibrillation at an initial energy setting suitable for defibrillating a patient of average impedance, then raise the energy setting for subsequent defibrillation attempts in the event that the initial setting failed. The repeated defibrillation attempts require additional energy and add to patient risk.

Some prior art defibrillators measure the patient impedance, or a parameter related to patient impedance, and alter the shape of a subsequent defibrillation shock based on the earlier measurement. For example, the implanted defibrillator described in the Fain patent delivers a defibrillation shock of predetermined shape to the patient's heart in response to a detected arrhythmia. The Fain device measures the system impedance during delivery of that shock and uses the measured impedance to alter the shape of a subsequently delivered shock.

Another example of the measurement and use of patient impedance information in prior art defibrillators is described in an article written by R. E. Kerber, et al., "Energy, current, and success in defibrillation and cardioversion," *Circulation* (May 1988). The authors describe an external defibrillator that administers a test pulse to the patient prior to administering the defibrillation shock. The test pulse is used to measure patient impedance; the defibrillator adjusts the amount of energy delivered by the shock in response to the measured patient impedance. The shape of the delivered waveform is a damped sinusoid.

Prior art disclosures of the use of truncated exponential biphasic waveforms in implantable defibrillators have provided little guidance for the design of an external defibrillator that will achieve acceptable defibrillation or cardioversion rates across a wide population of patients. The defibrillator operating voltages and energy delivery requirements affect the size, cost, weight and availability of components. In particular, operating voltage requirements affect the choice of switch and capacitor technologies. Total energy delivery requirements affect defibrillator battery and capacitor choices. Thus, even if an implantable defibrillator and an external defibrillator both deliver waveforms of similar shape, albeit with different waveform amplitudes, the actual designs of the two defibrillators would be radically different.

SUMMARY OF THE INVENTION

This invention provides a defibrillator and defibrillation method that automatically compensates for patient-to-patient differences in the delivery of electrotherapeutic pulses for defibrillation and cardioversion. The defibrillator has an energy source that may be discharged through electrodes to administer a truncated exponential biphasic voltage or current pulse to a patient.

The preferred embodiment of the method comprises the steps of charging the energy source to an initial level; discharging the energy source across the electrodes to deliver electrical energy to the patient in a multiphasic waveform; monitoring a patient-dependent electrical parameter during the discharging step; shaping the waveform of the delivered electrical energy based on a value of the monitored electrical parameter, wherein the relative duration of the phases of the multiphasic waveform is dependent on the value of the monitored electrical parameter.

The preferred apparatus comprises an energy source; two electrodes adapted to make electrical contact with a patient; a connecting mechanism forming an electrical circuit with the energy source and the electrodes when the electrodes are attached to a patient; and a controller operating the connecting mechanism to deliver electrical energy from the energy source to the electrodes in a multiphasic waveform the relative phase durations of which are based on an electrical parameter monitored during delivery of the electrical energy. The preferred defibrillator apparatus weighs less than 4 pounds and has a volume less than 150 cubic inches, and most preferably, weighs approximately three pounds or less and has a volume of approximately 141 cu. in.

DETAILED DESCRIPTION OF THE PREFERRED EMBODIMENT

For any given patient and for any given defibrillator system design, whether implantable or external, there is an optimal biphasic waveform for treating a particular kind of arrhythmia. This principle is used when implanting defibrillators; as noted above, implanted defibrillators are titrated to the patient at the time of implant. External defibrillators, on the other hand, must be designed to be effective in a wide population of patients.

Figure 1:
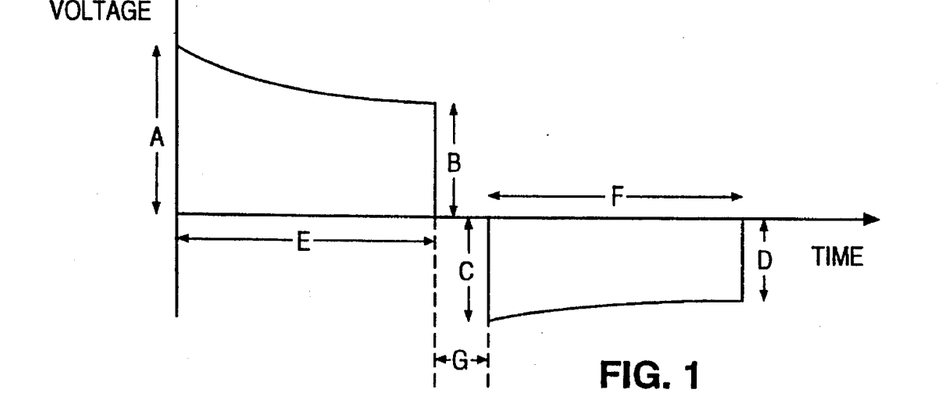
FIG. 1 is a schematic representation of a low-tilt biphasic electrotherapeutic waveform.
Figure 2:
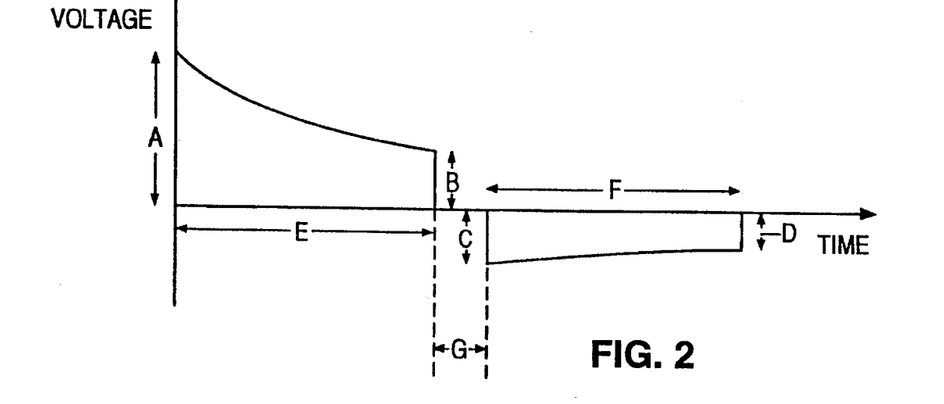
FIG. 2 is a schematic representation of a high-tilt biphasic electrotherapeutic waveform.

For example, FIGS. 1 and 2 illustrate the patient-to-patient differences that an external defibrillator design must take into account. These figures are schematic representations of truncated exponential biphasic waveforms delivered to two different patients from an external defibrillator according to the electrotherapy method of this invention for defibrillation or cardioversion. In these drawings, the vertical axis is voltage, and the horizontal axis is time. The principles discussed here are applicable to waveforms described in terms of current versus time as well.

The waveform shown in FIG. 1 is called a low-tilt waveform, and the waveform shown in FIG. 2 is called a high-tilt waveform, where tilt H is defined as a percent as follows:

$$H = \frac{|A| - |D|}{|A|} \times 100$$

As shown in FIGS. 1 and 2, A is the initial first phase voltage and D is the second phase terminal voltage. The first phase terminal voltage B results from the exponential decay over time of the initial voltage A through the patient, and the second phase terminal voltage D results from the exponential decay of the second phase initial voltage C in the same manner. The starting voltages and first and second phase durations of the FIG. 1 and FIG. 2 waveforms are the same; the differences in end voltages B and D reflect patient differences.

We have determined that, for a given patient, externally-applied truncated exponential biphasic waveforms defibrillate at lower voltages and at lower total delivered energies than externally-applied monophasic waveforms. In addition, we have determined that there is a complex relationship between total pulse duration, first to second phase duration ratio, initial voltage, total energy and total tilt in the delivery of an effective cardioversion waveform. Thus, it is possible to design a defibrillator and defibrillation method that is effective not only for a single patient (as in most prior art implantable defibrillators) but is also effective for a broad population of patients. In addition, it is also possible to meet external defibrillator design requirements regarding the size, weight and capacity of the defibrillator energy source while still meeting the needs of a wide patient population.

Up to a point, the more energy delivered to a patient in an electrotherapeutic pulse, the more likely the defibrillation attempt will succeed. Low-tilt biphasic waveforms achieve effective defibrillation rates with less delivered energy than high-tilt waveforms. However, low-tilt waveforms are energy inefficient, since much of the stored energy is not delivered to the patient. On the other hand, defibrillators delivering high-tilt biphasic waveforms deliver more of the stored energy to the patient than defibrillators delivering low-tilt waveforms while maintaining high efficacy up to a certain critical tilt value. Thus, for a given capacitor, a given initial voltage and fixed phase durations, high impedance patients receive a waveform with less total energy and lower peak currents but better conversion properties per unit of energy delivered, and low impedance patients receive a waveform with more delivered energy and higher peak currents.

There appears to be an optimum tilt range in which high and low impedance patients will receive effective and efficient therapy from an external defibrillator. An optimum capacitor charged to a predetermined voltage can be chosen to deliver an effective and efficient waveform across a population of patients having a variety of physiological differences. For example, the defibrillator may operate in an open loop, i.e., without any feedback regarding patient parameters and with preset pulse phase durations which will be effective for a certain range of patients. The preset parameters of the waveforms shown in FIG. 1 and 2 are therefore the initial voltage A of the first phase of the pulse, the duration E of the first phase, the interphase duration G, and the duration F of the second phase. The terminal voltage B of the first phase, the initial voltage C of the second phase, and the terminal voltage D of the second phase are dependent upon the physiological parameters of the patient and the physical connection between the electrodes and the patient.

For example, if the patient impedance (i.e., the total impedance between the two electrodes) is high, the amount of voltage drop (exponential decay) from the initial voltage A to the terminal voltage B during time E will be lower (FIG. 1) than if the patient impedance is low (FIG. 2). The same is true for the initial and terminal voltages of the second phase during time F. The values of A, E, G and F are set to optimize defibrillation and/or cardioversion efficacy across a population of patients. Thus, high impedance patients receive a low-tilt waveform that is more effective per unit of delivered energy, and low impedance patients receive a high-tilt waveform that delivers more of the stored energy and is therefore more energy efficient.

Figure 3:
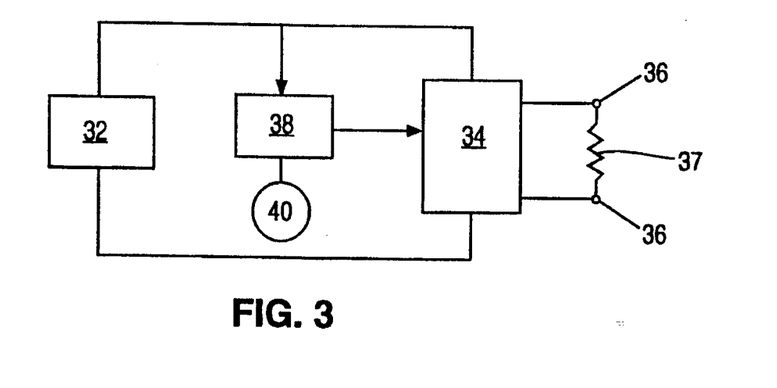
FIG. 3 is a block diagram of a defibrillator system according to a preferred embodiment of the invention.

In order to ensure that the delivered shock will be within the optimum tilt range for an extended range of patients, this invention provides a defibrillator method and apparatus for adjusting the characteristics of the defibrillator waveform in response to a real-time measurement of a patient-dependent electrical parameter. FIG. 3 is a block diagram showing a preferred embodiment of the defibrillator system.

The defibrillator system 30 comprises an energy source 32 to provide a voltage or current pulse. In one preferred embodiment, energy source 32 is a single capacitor or a capacitor bank arranged to act as a single capacitor.

A connecting mechanism 34 selectively connects and disconnects a pair of electrodes 36 electrically attached to a patient (represented here as a resistive load 37) to and from the energy source. The connections between the electrodes and the energy source may be in either of two polarities with respect to positive and negative terminals on the energy source.

The defibrillator system is controlled by a controller 38. Specifically, controller 38 operates the connecting mechanism 34 to connect energy source 32 with electrodes 36 in one of the two polarities or to disconnect energy source 32 from electrodes 36. Controller 38 receives discharge information (such as current, charge and/or voltage) from the discharge circuit. Controller 38 may also receive timing information from a timer 40.

Controller 38 uses information from the discharge circuit and/or the timer to control the shape of the waveform delivered to the patient in real time (i.e., during delivery of the waveform), such as by selecting appropriate waveform parameters from a memory location associated with the controller or by otherwise adjusting the duration of the phases of the biphasic waveform. By controlling the waveform shape, the system controls the duration, tilt and total delivered energy of the waveform. For example, biphasic waveforms with relatively longer first phases have better conversion properties than waveforms with equal or shorter first phases, provided the total duration exceeds a critical minimum. Therefore, in the case of high impedance patients, it may be desirable to increase the duration of the first phase of the biphasic waveform relative to the duration of the second phase to increase the overall efficacy of the electrotherapy by delivering a more efficacious waveform and to increase the total amount of energy delivered.

Figure 4:
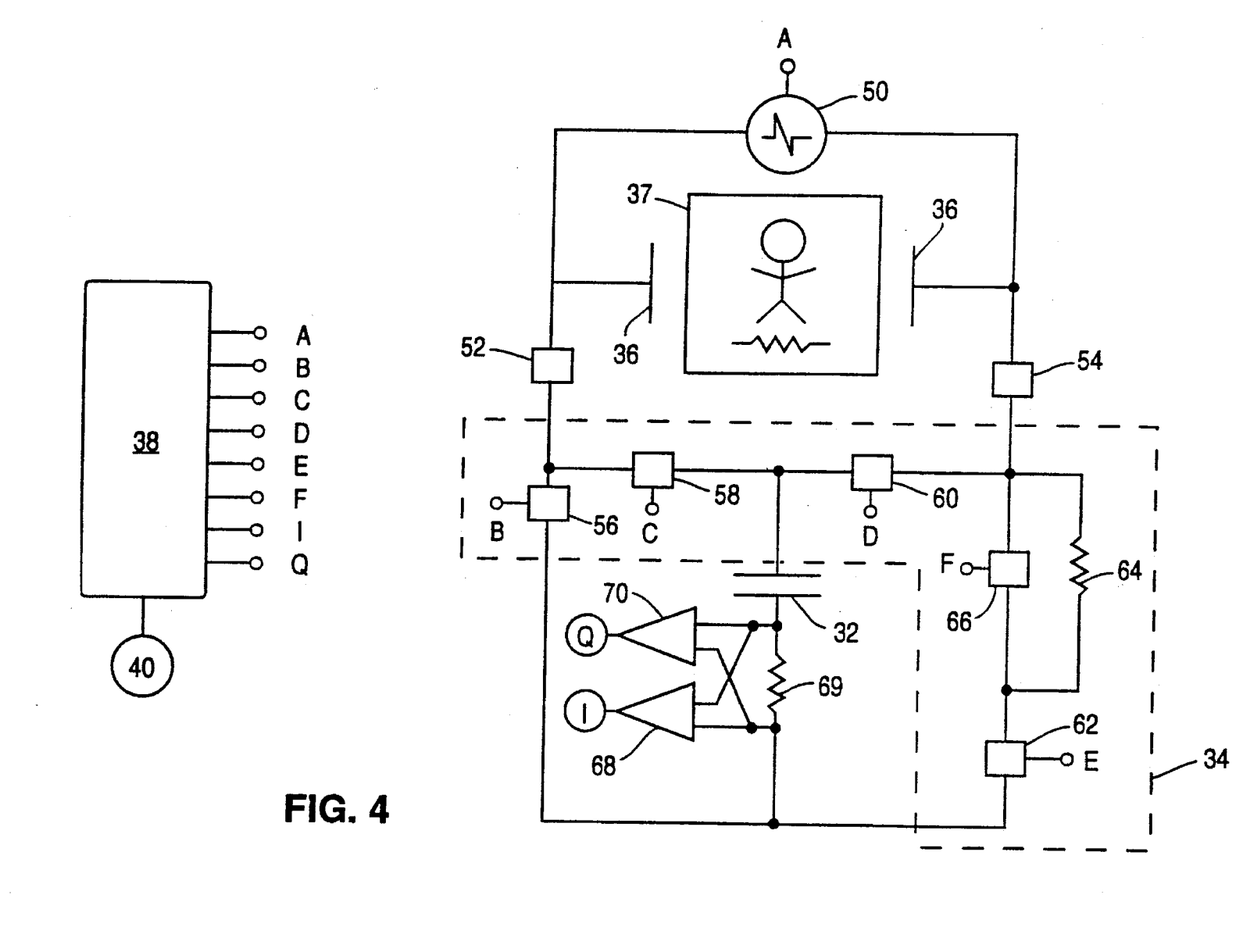
FIG. 4 is a schematic circuit diagram of a defibrillator system according to a preferred embodiment of this invention.

A preferred embodiment of a defibrillator system according to the invention is shown schematically in FIG. 4. In this diagram, the energy source is a capacitor 32 preferably having a size between 60 and 150 microfarads, most preferably 100 microfarads. The system also includes a charging mechanism (not shown) for charging the capacitor to an initial voltage.

A controller 38 controls the operation of the defibrillator to deliver a shock to the patient 37 through electrodes 36 automatically in response to a detected arrhythmia or manually in response to a human operator. FIG. 4 shows an ECG system 50 attached to the electrodes to provide ECG monitoring and/or arrhythmia detection. FIG. 4 also shows a pair of switches 52 and 54 isolating the patient and the ECG system from the defibrillation circuitry. Switches 52 and 54 may be any suitable kind of isolators, such as mechanical relays, solid state devices, spark gaps, or other gas discharge devices. The ECG system and the isolation switches are not essential parts of this invention.

In this embodiment, the connecting mechanism 34 includes four switches 56, 58, 60 and 62 operated by the controller 38 to deliver a shock from the energy source 32 to the patient. The preferred embodiment also may include an optional current limiting circuit comprising a resistor 64 and switch 66 to provide additional protection to the defibrillator circuit components and to the defibrillator operator. The operation of the isolation switches and the connecting mechanism to deliver a waveform to the patient is described below.

For purposes of this description, it is assumed that all switches are open prior to discharge. It should be understood that this need not be the case. For example, switches 56, 62 and 66 could start out in the closed position, with the operating sequence of the switches modified accordingly.

In response to a request for a shock, the controller first closes switches 52 and 54, then switch 62, then switch 58 to initiate delivery of a limited shock to the patient. A current sensor 68 monitors the current delivered by the capacitor. If the peak current is below a circuit safety threshold, then switch 66 is closed to take safety resistor 64 out of the circuit. Peak current values above the threshold could indicate a short circuit condition.

In the preferred embodiment, the duration of the first and second phases of the biphasic waveform are determined by measuring a patient-dependent electrical parameter. As described in more detail below, the measured parameter in the preferred embodiment is the time it takes for a predetermined amount of charge to be delivered by the energy source to the patient. Charge control can provide better noise immunity than other waveform monitoring methods, such as voltage or current monitoring.

The system shown in FIG. 4 uses a current integrator 70 to provide charge information to the controller. The controller sets the duration of the first and second waveform phases (thereby controlling the waveform shape) based on charge information from current integrator 70. Other means of determining phase durations may be used, of course, without departing from the scope of the invention.

At the end of the first phase of the waveform, the controller opens switch 62 to terminate delivery of the shock. Switch 66 may also be opened at any time from this point on. The controller opens switch 58 as well.

After the lapse of a brief interphase period, the controller closes switches 56 and 60 to initiate delivery of the second phase of the waveform. In the preferred embodiment the second phase duration is determined by the first phase duration. Other means of determining second phase duration are within the scope of the invention, however. At the end of the second phase, the controller opens switch 56 to terminate delivery of the shock. Switches 60, 52 and 54 are opened thereafter.

The following example illustrates a specific implementation of the method and apparatus of this invention. The invention is not limited to the values and circuit elements discussed in this example.

In this example, switches 52 and 54 are implemented as a double pole, double throw mechanical relay. Switches 58 and 60 are each implemented as a pair of SCR's in series in order to meet required standoff voltages with currently available components. Switch 56 is implemented as two insulated gate bipolar transistors ("IGBT's") in series, again due to high voltage requirements.

The functions of switches 66 and 62 are shared among three IGBT's to meet voltage standoff requirements, with one IGBT being on at the same time as switch 66 and off at the same time as switch 62. In this implementation resistor 64 is split into two resistors to equally divide the voltage across the IGBT's.

The current sensor 68 may be used to send current information to the controller for purposes of, e.g., short circuit protection, leads off detection, etc. The manner in which the short circuit or leads off conditions are detected are beyond the scope of this invention. The integrator 70 and current sensor 68 may each be an op-amp feeding a threshold comparator for detecting charge and Current limits, respectively. The integrator could be provided with a switch for resetting to initial conditions prior to a waveform delivery.

A comparator associated with the current integrator monitors the charge delivered to the patient and sends a signal to the waveform controller when the charge reaches 0.06182 Coulombs (referred to as "Qt"). The time required to reach that charge ("t(Qt)") is monitored by the controller using an up/down counter which counts a scaled down reference frequency. One element of the frequency scaler is a selectable 2:3 prescaler. The pre-scaler is set to 3 during the first phase. In this example, eleven time thresholds are stored in the controller, which determines the first phase duration ("t(Φ1)") based on the time required to reach Qt. At each time threshold, a new value of t(Φ1) is loaded until Qt is reached. If Qt is not reached within 6.35 mS, then t(Φ1) is set to 12 mS. The counter runs at the scaled down frequency during delivery of the entire first phase.

Some exemplary values for Qt thresholds and t(Φ1) are shown in Table I.

TABLE I

| If t (Qt) < (mS) | Then t (φ1) is (mS) |
|---|---|
| 1.13 | 2.3 |
| 1.60 | 2.85 |
| 2.07 | 3.79 |
| 2.56 | 4.02 |
| 3.07 | 4.83 |
| 3.58 | 6.76 |
| 4.10 | 7.73 |
| 4.64 | 8.69 |
| 5.20 | 9.66 |
| 5.77 | 10.62 |
| 6.35 | 11.59 |

In this example, the interphase delay is set at 300 µS. At 0 µS the first phase IGBT's are opened, terminating the first phase. At 250 µS, the second phase IGBT's are closed. At 300 µS the second phase SCR's are closed, initiating the second phase.

In this example, second phase timing is determined by first phase timing. Specifically, the count value accumulated during phase one (2.3 mS to 12 mS) is used to control the duration of the second phase. During the second phase, the counter that had been counted up during the first phase is counted down to 0, at which time the second phase is terminated. The actual duration of the second phase depends on the scaled down frequency used to run down the counter. If the first phase t(Qt) was less than 3.07 mS, then the reference clock prescaler is set to 3 to a give second phase duration equal to the first phase duration. If t(Qt) is greater than or equal to 3.07 mS, then the pre-scaler is set to 2, giving a second phase duration which is ⅔ of the first phase duration.

In an alternative embodiment, the measured patient-dependent electrical parameter is capacitor voltage. A comparator monitors the capacitor voltage and sends a signal to the waveform controller when the voltage decays to 1000 volts (Vt). As in the charge control embodiment, the time required to reach that voltage is monitored by the controller using an up/down counter which counts a scaled down reference frequency. The first phase duration (t(Φ1)) is based on the time required to reach Vt. The method of selecting the appropriate t(Φ1) is identical to the charge control embodiment. If Vt is not reached within 6.18 mS, then t(Φ1) is set to 12 mS. Table II shows the t(Vt) thresholds and their associated t(Φ1).

TABLE II

| If t (Vt) < (mS) | Then t (φ1) is (mS) |
|---|---|
| 1.24 | 2.3 |
| 1.73 | 2.85 |
| 2.23 | 3.79 |
| 2.72 | 4.02 |
| 3.22 | 4.83 |
| 3.71 | 6.76 |
| 4.20 | 7.73 |

TABLE II-continued

| If t (Vt) < (mS) | Then t (φ1) is (mS) |
|---|---|
| 4.70 | 8.69 |
| 5.19 | 9.66 |
| 5.69 | 10.62 |
| 6.18 | 11.59 |

Interphase delay and second phase timing is identical to the charge control method.

We have designed a new defibrillator meeting certain size, weight, efficacy and safety design goals. The size and weight are below the design thresholds of 150 cu. in. and four lbs. This new portable defibrillator may therefore be carried and stored in places such as drug kit boxes carried by early medical responders and in the glove boxes of cars.

The circuit design of the new defibrillator permits the use of a biphasic truncated exponential waveform, such as one of the waveforms described above. Use of the biphasic waveform permits the defibrillator to be operated with the same efficacy as prior art external defibrillators but with the storage and delivery of far less energy at lower voltages. For example, the new defibrillator effectively cardioverts patients by delivering shocks below 155 Joules of energy (167 Joules of energy stored), and most preferably on the order of 130 Joules of energy (140 Joules stored), compared with the delivery of 200–360 Joules (240–439 Joules stored) by prior art external defibrillators.

Figure 5:
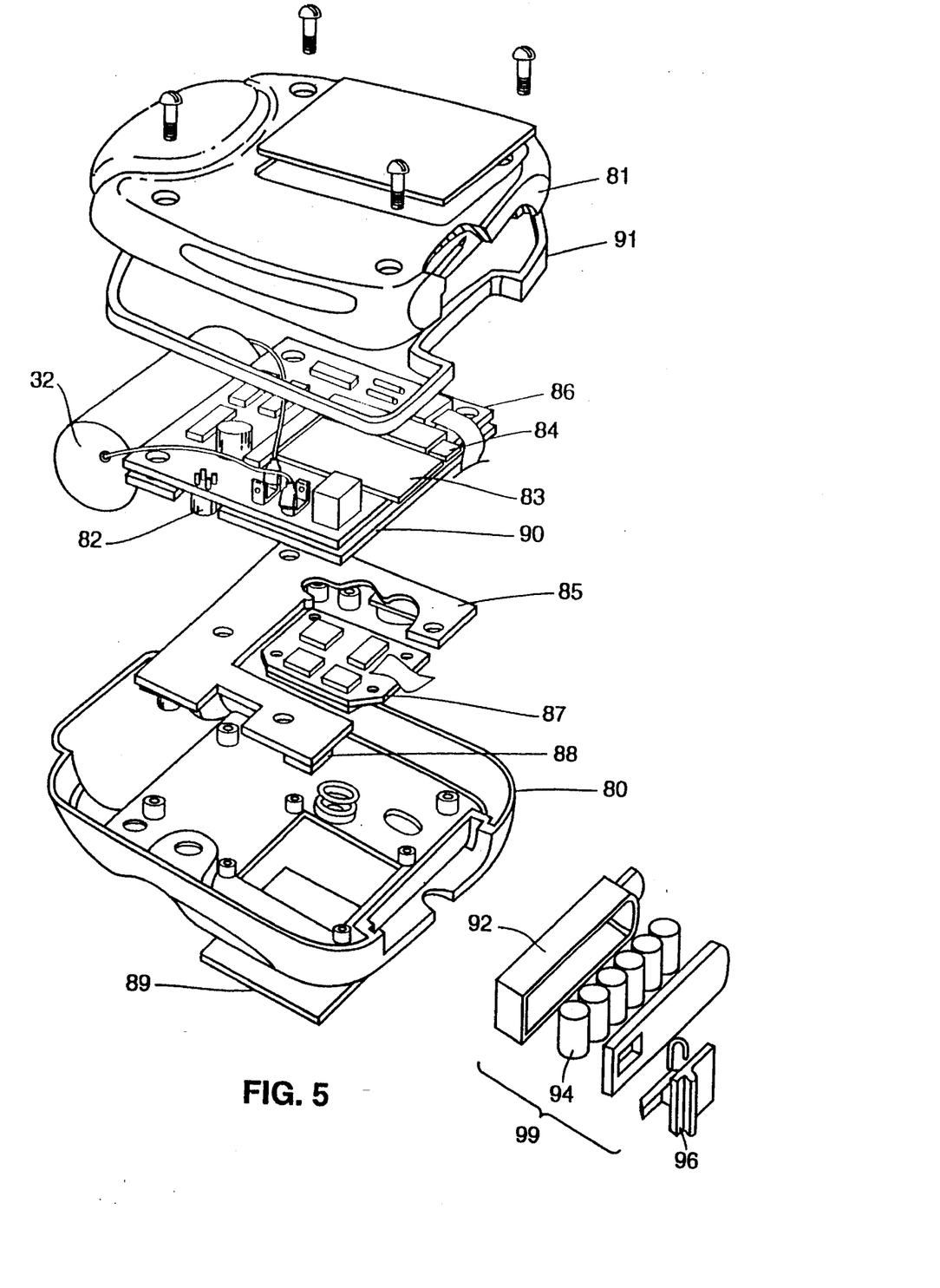
FIG. 5 is an external view of a defibrillator according to a preferred embodiment of this invention.
Figure 6:
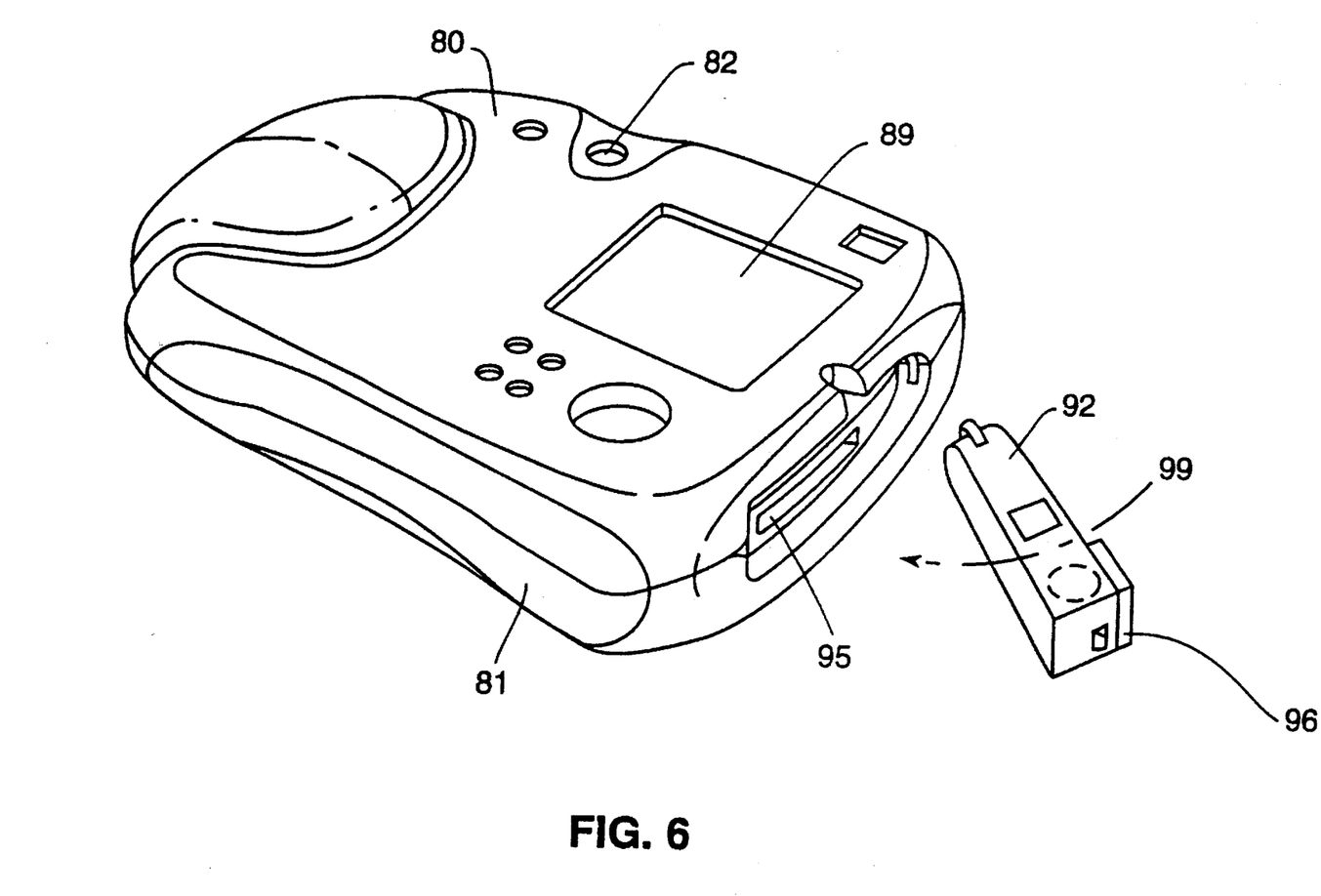
FIG. 6 is a partial cutaway view of a defibrillator according to a preferred embodiment of this invention.

A preferred embodiment of the new external defibrillator is shown in FIGS. 5 and 6. This defibrillator is much smaller and lighter than prior art external defibrillators. The size of the preferred defibrillator (approx. 2.2 in. ×8 in. ×8 in., for a total volume of approx. 141 cu. in.) permits it to be carried and/or stored in places in which prior art external defibrillators could not fit. In addition, its lighter weight (approx. three pounds) enables the defibrillator to be moved more easily by the operator in an emergency.

As shown in FIGS. 5 and 6, the preferred external defibrillator includes a molded two-part plastic housing with an upper case 80 and a lower case 81. A main printed circuit board ("PCB") 86 supports the capacitor 32, an electrode connector 82, a PCMCIA memory card 83 and a PCMCIA memory card ejector mechanism 84. The PCMCIA memory card 83 lies within a PCMCIA memory card slot 95 on PCB 86.

A keyboard PCB 85 and a display PCB 87 is disposed between the main PCB 86 and the upper case 80. Keyboard PCB 85 interfaces with the defibrillator's operator buttons, and display PCB 87 operates the defibrillator's LCD display 88. A display window 89 in the upper case permits display 88 to be seen by an operator.

An insulator 90 is disposed between main PCB 86 and display PCB 87. A sealing gasket 91 lines the edges between upper case 80 and lower case 81 when the housing is assembled.

A battery assembly 99 consisting of a battery housing 92 and six lithium-manganese dioxide primary cells 94 is disposed in upper case 80 so that the batteries are in electrical contact with the capacitor charge circuits and other circuits of main PCB 86. The battery assembly has a latching mechanism 96 for attaching and detaching the battery assembly to and from the defibrillator.

The location of the battery assembly in front of the PCMCIA memory card slot prevents the defibrillator operator or others from accessing the PCMCIA card while the defibrillator is powered up and operating. This arrangement protects the operator and patient from accidental shocks and protects the defibrillator itself from damage caused by inadvertent removal of the PCMCIA card during operation.

The small size and light weight of our defibrillator is due to a combination of a variety of design features. Use of a truncated exponential biphasic waveform instead of the prior art damped sinusoid waveform permits operation without an inductor in the waveform circuit. In addition, the lower energy requirements permit the use of a smaller capacitor and smaller batteries than those used in prior art external defibrillators.

In an effort to reduce the battery size even further, the preferred embodiment is provided with a capacitor precharge circuit and controller that begins charging the capacitor soon after the defibrillator is activated, even before ventricular fibrillation (and therefore the need for defibrillation) has been detected. The precharge voltage level is kept below the level where damage to the defibrillator circuit, the patient or the operator could occur in the event of a single fault. Thus, for example, whereas in the preferred embodiment the full preshock capacitor voltage is 1650 V, the precharge level is 1100 V. This precharge procedure minimizes the amount of energy that needs to be transferred from the battery to the capacitor when a therapeutic shock is indicated, thereby reducing the required size of the battery and the defibrillator's transformer.

The preferred embodiment uses 6 lithium-manganese dioxide primary cells instead of rechargeable batteries. Primary cells have greater energy density than rechargeable batteries and are cheaper, lighter and, since they are disposable, they are easier to maintain. While primary cells also have lower power and energy characteristics, use of a truncated exponential biphasic waveform and a capacitor precharge circuit permits operation at lower power levels.

The preferred defibrillator shown in FIGS. 5 and 6 incorporates the solid state defibrillator circuit described above with reference to FIG. 4. Use of this circuit along with the short-circuit protection feature described above also reduces the size and weight of the defibrillator by avoiding the use of the mechanical switches required by higher voltage devices.

Other smaller and lighter-weight features of the defibrillator shown in FIGS. 5 and 6 are the use of a flat panel LCD in place of the more conventional CRT display and the use of a PCMCIA memory card to record voice and instrument information instead of a magnetic tape recorder or a paper strip chart recorder. In addition, the preferred defibrillator includes a feature whereby part of the patient ECG information stored within the PCMCIA card can be displayed on the LCD for use by a medical professional. This feature takes the place of the strip chart recorders in prior art external defibrillators.

Lightweight defibrillator electrode designs may be used to reduce the weight of the overall device even further. For example, flexible patch electrodes may be used in place of the conventional paddle electrodes. In addition, because of the lower energy and voltage features of the defibrillator, relatively thin wires may be used to attach the electrodes to the defibrillator instead of thick cables.

Other component choices and other configurations of components are within the scope of this invention as long as the threshold size and weight requirements of 150 cu. in. and four pounds are met.

Any embodiment of this invention could provide for alternating initial polarities in successive monophasic or biphasic pulses. In other words, if in the first biphasic waveform delivered by the system the first phase is a positive voltage or current pulse followed by a second phase negative voltage or current pulse, the second biphasic waveform delivered by the system would be a negative first phase voltage or current pulse followed by a positive second phase voltage or current pulse. This arrangement would minimize electrode polarization, i.e., build-up of charge on the electrodes.

For each defibrillator method discussed above, the initial first phase voltage may be the same for all patients or it may be selected automatically or by the defibrillator user. For example, the defibrillator may have a selection of initial voltage settings, one for an infant, a second for an adult, and a third for use in open heart surgery.

In addition, while the preferred embodiment of the invention has been discussed in the context of biphasic waveforms, monophasic, triphasic or other multiphasic waveforms may be used as well. Also, patient-dependent electrical parameters other than charge delivered may be monitored and used to shape the waveform during discharge.

While the invention has been discussed with reference to external defibrillators, one or more aspects of the invention would be applicable to implantable defibrillators as well. Other modifications will be apparent to those skilled in the art.

We claim:

1. A method for applying electrotherapy to a patient through electrodes connected to an energy source, the method comprising the following steps:

charging the energy source to an initial level;

discharging the energy source across the electrodes to deliver electrical energy to the patient in a multiphasic waveform;

monitoring a patient-dependent electrical parameter during the discharging step;

shaping the waveform of the delivered electrical energy based on a value of the monitored electrical parameter, wherein the relative duration of the phases of the multiphasic waveform is dependent on the value of the monitored electrical parameter.

2. The method of claim 1 wherein the energy source is external to the patient.

3. The method of claim 1 wherein the shaping step further comprises controlling the duration of a waveform phase based on a value of the electrical parameter.

4. The method of claim 3 wherein the shaping step further comprises controlling the duration of another phase of the waveform based on the value.

5. The method of claim 4 further comprising the step of providing a plurality of phase duration values, the shaping step comprising the step of selecting phase duration values for each phase of the multiphasic waveform from the plurality of phase duration values.

6. The method of claim 3 wherein the electrical parameter is charge delivered by the energy source to one of the electrodes.

7. The method of claim 6 wherein the discharging step begins at a discharge start time, the method further comprising the step of monitoring elapsed time from the discharge start time, the shaping step further comprising the step of determining an elapsed time value at which the charge delivered has reached a predetermined threshold.

8. The method of claim 7 wherein the shaping step further comprises selecting a first phase duration based on the elapsed time value.

9. The method of claim 8 wherein the shaping step further comprises selecting a second phase duration based on the elapsed time value.

10. The method of claim 9 wherein the second phase duration is equal to the first phase duration for at least one possible elapsed time value.

11. The method of claim 9 wherein the second phase duration is less than the first phase duration for at least one possible elapsed time value.

12. The method of claim 1 wherein the duration of the monitoring step is shorter than the duration of the discharging step.

13. The method of claim 1 wherein the shaping step is performed without the use of an inductor.

14. The method of claim 1 wherein the initial level is an initial discharge level, the method further comprising the step of precharging the energy source to a level less than the initial discharge level prior to the step of charging the energy source to the initial discharge level.

15. A method for applying electrotherapy to a patient through electrodes connected to an energy source, the method comprising the following steps:

charging the energy source to an initial level;

discharging the energy source across the electrodes to deliver electrical energy to the patient in a truncated exponential biphasic waveform;

monitoring an electrical parameter during the discharging step;

adjusting the tilt of the waveform based on the value of the monitored electrical parameter, the adjusting step comprising controlling the duration of a waveform phase based on a value of the electrical parameter wherein the relative duration of the phases of the waveform is dependent on the value of the monitored electrical parameter.

16. An apparatus for administering electrotherapy to a patient's heart through electrodes external to the patient comprising:

an energy source;

two electrodes adapted to make electrical contact with a patient;

a connecting mechanism forming an electrical circuit with the energy source and the electrodes when the electrodes are attached to a patient; an electrical parameter monitor; and a controller operating the connecting mechanism to deliver electrical energy from the energy source to the electrodes in a truncated exponential multiphasic waveform the relative phase durations of which are based on an electrical parameter monitored during delivery of the electrical energy.

17. The apparatus of claim 16 wherein the connecting mechanism comprises a plurality of switches for selectively directing electrical energy from the energy source to the patient in one of two polarities.

18. The apparatus of claim 17 wherein the electrical parameter monitor comprises a charge sensor providing information to the controller related to charge delivered by the energy source to the electrodes.

19. The apparatus of claim 18 further comprising a timer associated with the charge sensor and the controller.

20. The apparatus of claim 19 wherein the controller comprises a counter with a controllable counting rate, the counter being adapted to count in one direction during delivery of a first phase of the multiphasic waveform and in another direction during delivery of a second phase of the multiphasic waveform.

21. The apparatus of claim 16 further comprising means for selectively limiting current flow through the electrodes and means for determining whether current flowing to the electrodes is below a predetermined threshold.

22. The apparatus of claim 21 wherein the means for selectively limiting current flow comprises an impedance and a shunting switch in the circuit with the electrodes and the energy source.

23. The apparatus of claim 16 wherein the energy source comprises a battery disposed in a battery holder, the apparatus further comprising a solid state memory device disposed in a memory device holder, the battery blocking external access to the memory device when the battery is disposed in the battery holder.

24. An external defibrillator comprising:

an energy source;

two electrodes adapted to make electrical contact with the exterior of a patient;

a connecting mechanism forming an electrical circuit with the energy source and the electrodes when the electrodes are attached to a patient;

a controller operating the connecting mechanism to deliver electrical energy from the energy source to the electrodes; and a housing containing at least the energy source, the connecting mechanism and the controller, the housing having a volume less than 150 cubic inches.

25. The defibrillator of claim 24 in which the housing has a first dimension not greater than 2.2 inches.

26. The defibrillator of claim 25 in which the housing has second and third dimensions not greater than 8 inches.

27. The defibrillator of claim 24 wherein the energy source comprises primary cell batteries.

28. The defibrillator of claim 27 wherein the primary cell batteries comprise lithium-manganese dioxide primary batteries.

29. The defibrillator of claim 24 wherein the connecting mechanism and the controller comprise means for delivering a multiphasic waveform without the use of an inductor.

30. The defibrillator of claim 24 wherein the energy source comprises a capacitor, the defibrillator further comprising a capacitor precharge circuit.

31. The defibrillator of claim 24 further comprising an ECG system.

32. The defibrillator of claim 31 further comprising an LCD display.

33. The defibrillator of claim 32 further comprising a PCMCIA memory card.

34. The defibrillator of claim 33 further comprising means for displaying ECG information stored in the PCMCIA card on the LCD display.

35. The defibrillator of claim 24 wherein the energy source comprises a capacitive energy source sized between 60 and 150 microfarads.

36. An external defibrillator comprising:

an energy source;

two electrodes adapted to make electrical contact with the exterior of a patient;

a connecting mechanism forming an electrical circuit with the energy source and the electrodes when the electrodes are attached to a patient;

a controller operating the connecting mechanism to deliver electrical energy from the energy source to the electrodes;

the defibrillator having a weight less than four pounds.

37. The defibrillator of claim 36 wherein the energy source comprises primary cell batteries.

38. The defibrillator of claim 37 wherein the primary cell batteries comprise lithium-manganese dioxide primary batteries.

39. The defibrillator of claim 36 wherein the connecting mechanism and the controller comprise means for delivering a multiphasic waveform without the use of an inductor.

40. The defibrillator of claim 36 wherein the energy source comprises a capacitor, the defibrillator further comprising a capacitor precharge circuit.

41. The defibrillator of claim 36 further comprising an ECG system.

42. The defibrillator of claim 41 further comprising an LCD display.

43. The defibrillator of claim 42 further comprising a PCMCIA memory card.

44. The defibrillator of claim 43 further comprising means for displaying ECG information stored in the PCMCIA card on the LCD display.

45. The defibrillator of claim 36 wherein the energy source comprises a capacitive energy source sized between 60 and 150 microfarads.

46. A method for applying electrotherapy to a patient from an energy source external to the patient, the method comprising the following steps:

charging the energy source to an initial level;

discharging the energy source to deliver electrical energy to the patient in a multiphasic waveform;

determining the time during which a predetermined amount of charge is delivered to the patient;

shaping the waveform of the delivered electrical energy based on the value of the determined time, wherein the relative duration of the phases of the multiphasic waveform is dependent on the value of the determined time.

47. A method for applying electrotherapy to a patient through electrodes connected to an energy source, the method comprising the following steps:

charging the energy source to an initial level;

maintaining the charge of the energy source at the initial level;

determining the need to apply a shock to a patient;

charging the energy source to a second level greater than the initial level;

discharging the energy source across the electrodes to deliver electrical energy to the patient.

48. The method of claim 47 wherein the initial level is below a charge level that could harm a patient.

49. The method of claim 47 wherein the first charging step is performed in response to activation of a defibrillator.

50. The method of claim 47 wherein the discharging step comprises the step of discharging the energy source across the electrodes to deliver electrical energy to the patient in a truncated exponential biphasic waveform.

51. A method for applying electrotherapy to a patient through electrodes connected to an energy source, the method comprising the following steps:

charging the energy source to an initial level;

discharging the energy source across the electrodes to deliver electrical energy to the patient in a waveform, the patient and an additional impedance forming an electrical circuit with the energy source;

monitoring an electrical parameter during the discharging step;

removing the additional impedance from the electrical circuit if the electrical parameter is within a defined range prior to the end of the discharging step.

52. The method of claim 51 wherein the removing step comprises operating a switch associated with the additional impedance.

53. A method for applying electrotherapy to a patient comprising the following steps:

discharging an energy source across electrodes to deliver a waveform of electrical energy to the patient;

monitoring a patient-dependent electrical parameter during the discharge step;

ceasing the monitoring step prior to the end of the discharge step;

adjusting a waveform discharge parameter based on a value of the monitored parameter.

54. The method of claim 53 wherein discharging step and the monitoring step begin substantially simultaneously.

55. The method of claim 53 wherein the monitored parameter is time for delivering a predetermined quantity of charge to the patient.

56. The method of claim 55 wherein the discharge parameter is waveform duration.

57. The method of claim 55 wherein the waveform is a biphasic waveform and the discharge parameter is duration of a waveform phase.

58. A method for applying electrotherapy to a patient through electrodes attached to an energy source, the method comprising the following steps:

charging the energy source to an initial level prior to detecting a need to apply a shock to a patient;

determining the need to apply a shock to a patient;

charging the energy source to a second level greater than the initial level;

discharging the energy source across the electrodes to deliver electrical energy to the patient in a truncated exponential biphasic waveform.

59. The method of claim 58 wherein the first charging step is performed in response to activation of a defibrillator.

* * * * *

UNITED STATES PATENT AND TRADEMARK OFFICE
CERTIFICATE OF CORRECTION

PATENT NO. : 5,607,454
DATED : March 4, 1997
INVENTOR(S) : David Cameron, Thomas D. Lyster, Daniel J. Powers, Bradford E. Gliner, Clinton S. Cole, Carlton B. Morgan It is certified that error appears in the above-indentified patent and that said Letters Patent is hereby corrected as shown below:

On the title page: Item [56]

add to U.S. documents the following:

—5,411,526 5/1995 Kroll et al. 607/5
 5,334,430 9/1994 Berg et al. 607/7
 5,097,833 3/1992 Campos 607/46 —

Signed and Sealed this

Eleventh Day of November, 1997

Attest:

BRUCE LEHMAN

*Attesting Officer*   *Commissioner of Patents and Trademarks*